United States Patent
Thibodo, Jr.

[11] Patent Number: 5,947,915
[45] Date of Patent: Sep. 7, 1999

[54] SPLINT SYSTEM FOR ONE DIGIT OF THE HAND

[76] Inventor: Calvin Thibodo, Jr., 1061 Grandview Blvd., Kansas City, Kans. 66102

[21] Appl. No.: 08/818,959

[22] Filed: Mar. 14, 1997

[51] Int. Cl.⁶ .................................................. A61F 5/00
[52] U.S. Cl. ................................................. 602/5; 602/22
[58] Field of Search ............................. 602/5, 22, 21; 128/880, 879; 473/61, 60, 205, 212; 2/21

[56] References Cited

U.S. PATENT DOCUMENTS

| | | | |
|---|---|---|---|
| 4,103,682 | 8/1978 | Franzl | 602/22 |
| 4,765,320 | 8/1988 | Lindemann et al. | |
| 4,781,178 | 11/1988 | Gordon | 602/22 |
| 4,862,877 | 9/1989 | Barber | |
| 5,027,802 | 7/1991 | Donohue | |
| 5,267,945 | 12/1993 | Doctor et al. | 602/14 |
| 5,333,605 | 8/1994 | Matsumura et al. | 601/40 |
| 5,725,490 | 3/1998 | Conran | 602/21 |

OTHER PUBLICATIONS

Zimmer, Fracture Appliances, p. 91, 1947.

*Primary Examiner*—Richard J. Apley
*Assistant Examiner*—Kim M. Lee

[57] ABSTRACT

A splint system includes a splint body for one or more digits of a hand with the splint member for any particular finger having an extension member with a depending tongue that is received in a receiving channel formed in the end of the splint body portion of the splint for a particular finger. The fingers may be splinted along a straight line or with one or more phalanges bent at an angle to the general normal axis of a finger.

9 Claims, 5 Drawing Sheets

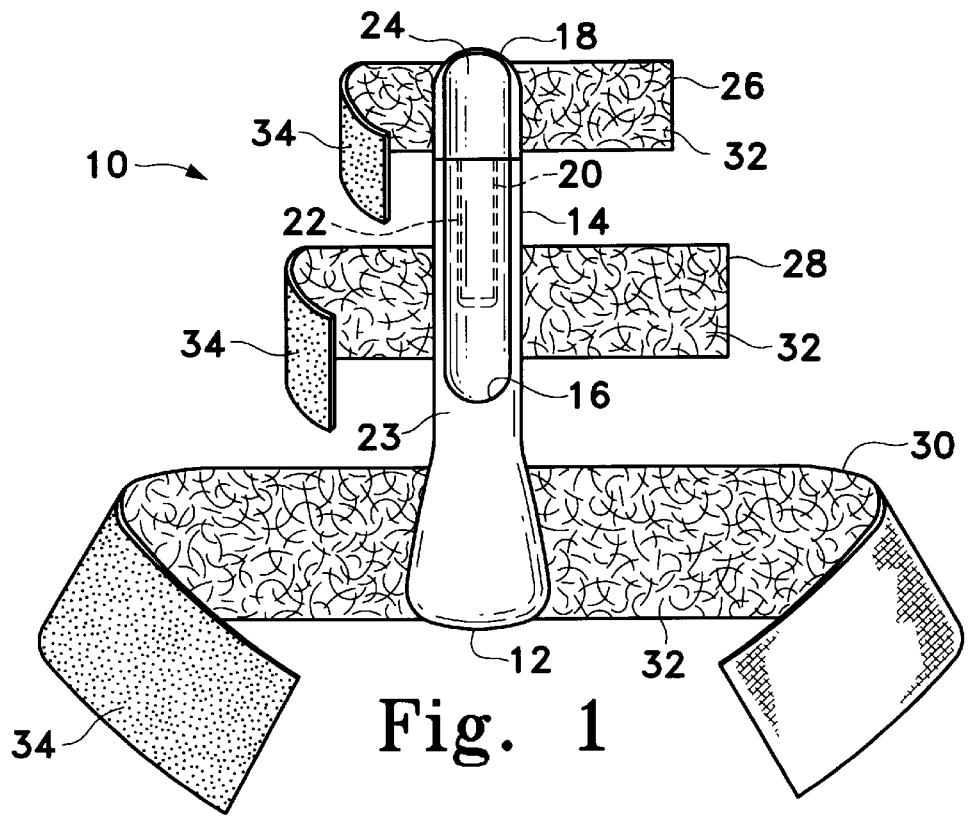
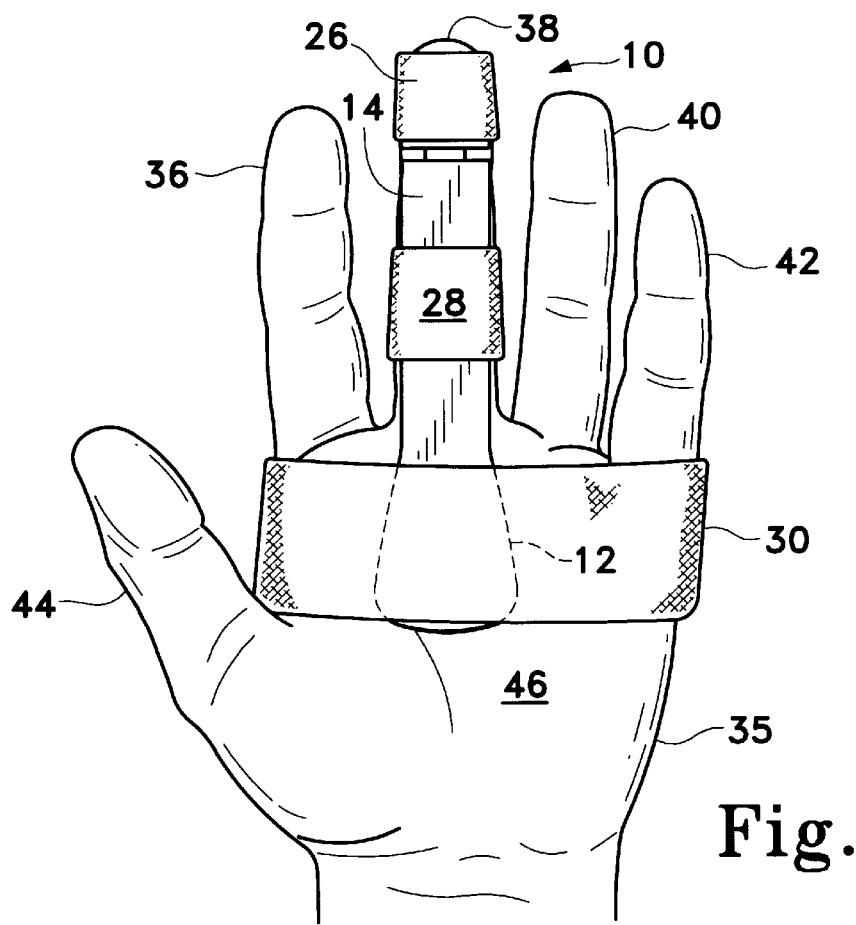

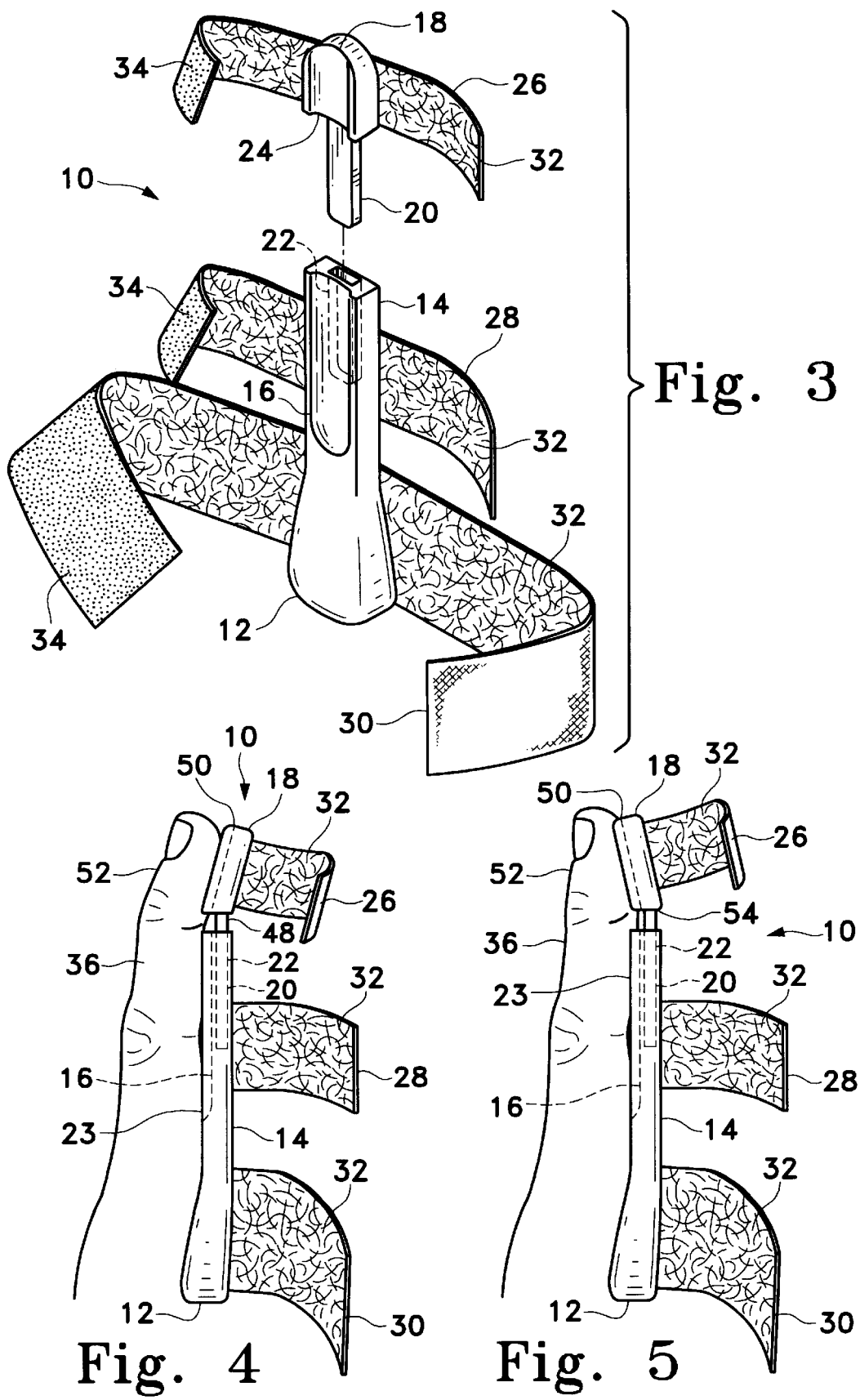

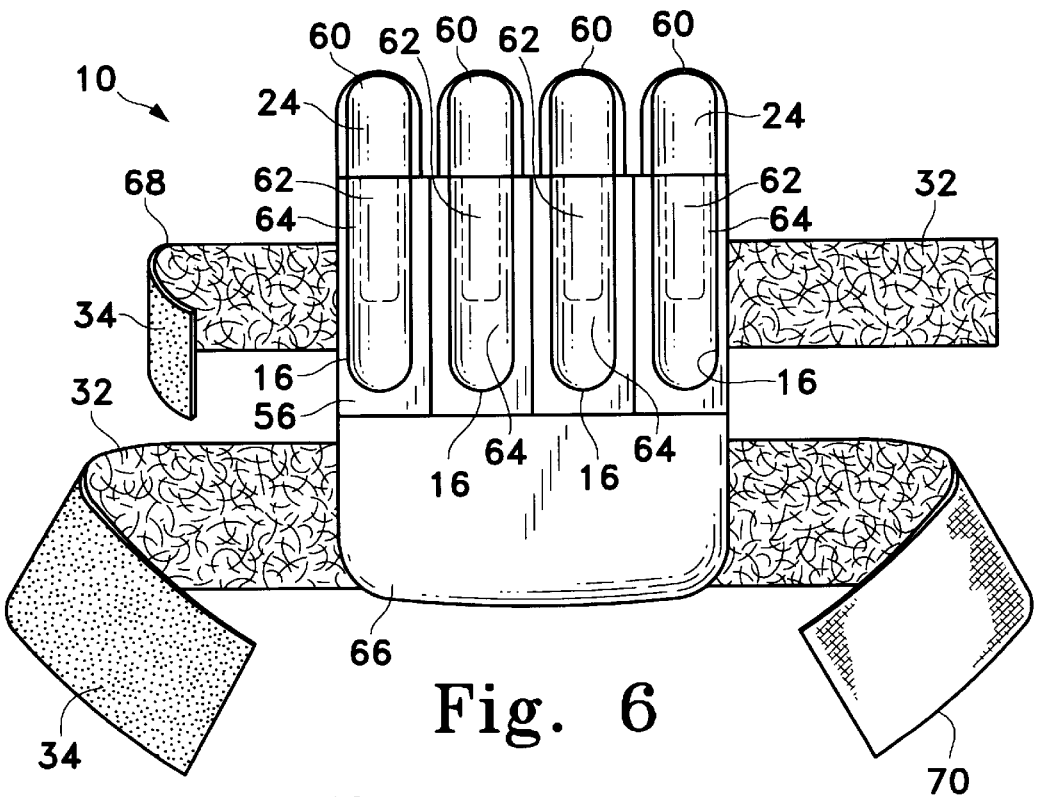
Fig. 6
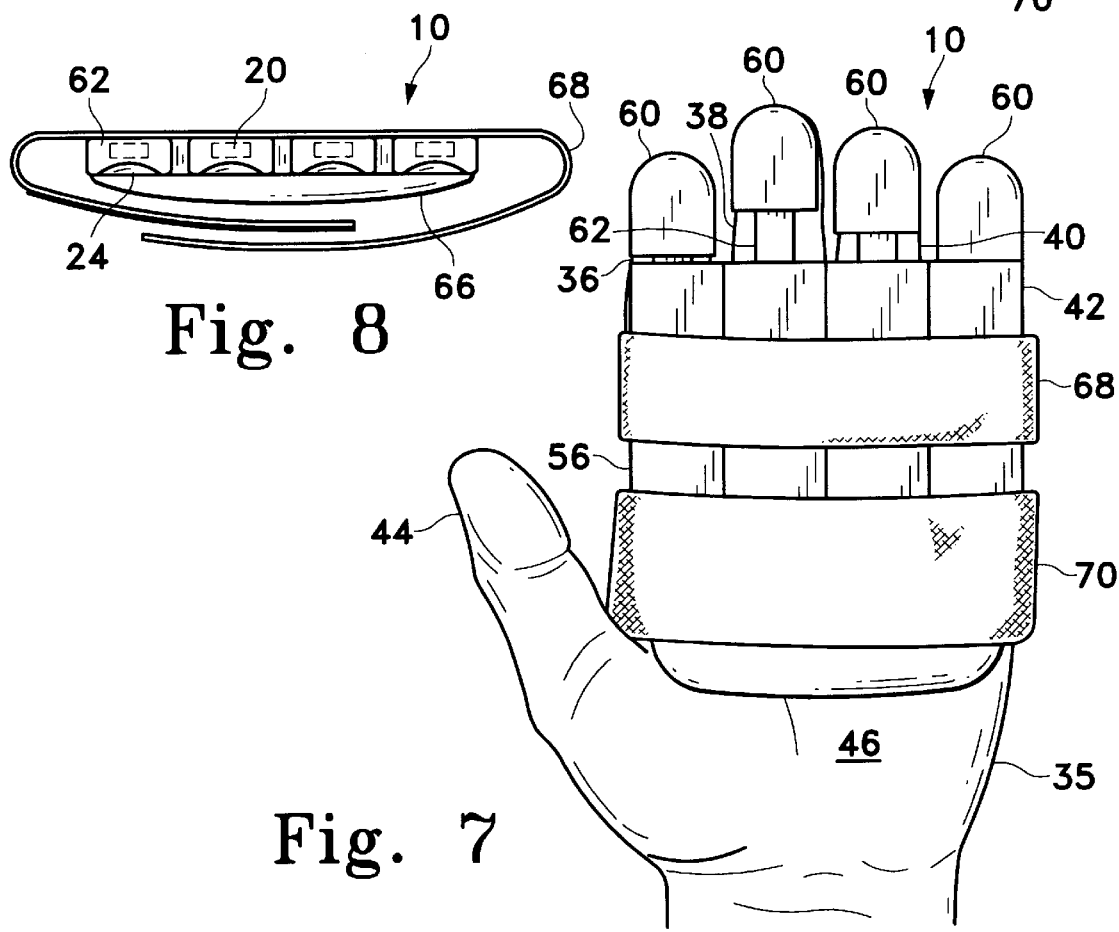
Fig. 8
Fig. 7

SPLINT SYSTEM FOR ONE DIGIT OF THE HAND

BACKGROUND OF THE INVENTION

1. Field of the Invention

The present invention is related to an apparatus for splinting fingers or thumbs. More particularly, the present invention is directed to a splinting system that is easily adaptable for fingers of different lengths.

2. Description of Related Art Including Information Disclosed Under 37 C.F.R. Sections 1.97–1.99

Injuries to fingers and hands are common and typical causes include trauma causing broken bones, strained ligaments and tendons and the like, carpal tunnel syndrome, repetitive motion injury, and the like. Frequently treatment requires that the affected finger or fingers be immobilized with a splint.

Prior art splints are typically either very simple or very complex. Simple splints include, for example, straight flat wooden or metal sticks that are bound to the affected fingers. Such splints do not allow a finger to be bent in any particular manner, merely holding the finger straight. In some cases proper healing requires that the affected finger or fingers be bent at one or more knuckles, either upwardly or downwardly, which cannot be as readily accomplished with a straight splint. Moreover, such splints do not conform with the basically cylindrical shape of the fingers and are therefore not comfortable and cannot be securely attached to the finger or fingers.

Other simple splints are formed from bent metal, such as aluminum, and may include an elongated trough shape designed to fit more closely to the finger and may include a curved upper end designed to protect a finger tip. Foam padding may be attached to the inner surface of such a splint. This type of splint, however, also holds the finger in a straight position.

More complex splints are very complicated and have many parts, such as Lindemann et al. U.S. Pat. No. 4,756,230, Gordon U.S. Pat. No. 4,781,178 and Donohue U.S. Pat. No. 5,027,802. Lindemann '320, for example, includes a collar applied over each finger and are connected to a forearm band by an elastic band. Gordon '178 discloses an orthopedic glove with one or more splints affixed at selective locations to immobilize and join and/or the wrist of the hand and is designed to immobilize particular joints having arthritis. Donohue '802 discloses a traction system for fingers that includes a traction element under the fingers or hand. All of these devices are complex, expensive and adapted to highly specific and relatively unusual finger problems. They are not suitable for more typical strains and broken bones.

The splints discussed above do not easily allow the separate or combined splinting treatment of any desired number of fingers at one time with a single device. Nor do these devices embody a splint of adjustable length splints that therefore can be used with fingers of different lengths on either different patients or on different fingers of the same patient's hand.

Therefore, there is a need for a finger splint system that easily allows the separate or combined splinting treatment of any desired number of fingers at one time with a single device; that can be used with fingers of different lengths on either different patients or on different fingers of the same patients hand; that can be used for one or more fingers; that allows fingers to be splinted into the optimal position for healing; and that is easy to use.

SUMMARY OF THE INVENTION

Accordingly, it is a primary object of the present invention to provide a finger splint system for one or more fingers that easily allows the separate or combined splinting treatment of any desired number of fingers at one time with a single device;

It is another object of the present invention to provide a finger splint system for one or more fingers that can be used with fingers of different lengths on either different patients or on different fingers of the same patient's hand.

It is another object of the present invention to provide a finger splint system for one or more fingers that can be used for one or more fingers.

It is another object of the present invention to provide a finger splint system for one or more fingers that allows fingers to be splinted into the optimal position for healing.

It is another object of the present invention to provide a finger splint system for one or more fingers that is easy to use.

These objects are achieved by providing an elongated basically rectangularly shaped solid splint having a concave inner surface curved to fit over the essentially cylindrical shape of the finger, with a somewhat bulbous base at the bottom for fitting comfortably into the palm of the patient. An extension member at the tip includes an elongated tongue that fits into a matching slot in the top of the splint body.

In another embodiment, the upper tip of the splint is bent to require the upper phalange of the splinted finger to be bent either downwardly or upwardly of its normal position, as required by the medical condition being treated.

In another embodiment, four such splints are ganged together into a single unit for splinting four fingers. The individual splint members are frangible and can easily be removed from the body of the splint device if there is not need of any particular single splint in a particular application.

In another embodiment, the thumb finger in particular is splinted with a splint system having a relatively large palm pad and a straight angled member for supporting the thumb.

In another embodiment, the fingers are loosely splinted and restrained from curling excessively into the palm, which, particularly in older patients, can exacerbate a tendency for the tendons to shorten, resulting in permanent cramping of the fingers. This embodiment comprises a solid rounded block fitted into the palm with four grooves along an upper edge for seating and restraining the bases of the four fingers, excluding the thumb finger.

In all embodiments, the splint or splint system is held on the finger or hand by a series of straps, preferably three straps, that wrap around the hand and affected finger or fingers and are fastened to themselves. In the preferred embodiments, the straps are fastened to themselves with hook and loop type fasteners.

The splint system for one or more digits of the hand disclosed herein is conveniently made in three basic sizes, which are small, medium, and large, to accommodate different hands of substantially different sizes. The splint system is also provided with models that splint any two or any three fingers, as well as an embodiment for the four parallel fingers. That is, the index and middle finger; the middle and ring finger; and the ring finger and pinkie finger, as well as, for example the index finger and ring finger and other combinations can be splinted with a single device. This principle is also used to provide a splint for any combination of three parallel fingers, whether or not they are all adjacent to one another.

In this specification, the term digit may be used interchangeably with the terms finger or thumb.

Other objects and advantages of the present invention will become apparent from the following description taken in connection with the accompanying drawings, wherein is set forth by way of illustration and example, the preferred embodiment of the present invention and the best mode currently known to the inventor for carrying out his invention.

BRIEF DESCRIPTION OF THE DRAWINGS

FIG. 1 is rear elevation of an adjustable finger splint according to the present invention for any single finger.

FIG. 2 is a front elevation of the finger splint of FIG. 1 shown installed on the middle finger of a hand (palm side toward viewer).

FIG. 3 is a right-hand front perspective view of the splint of FIG. 1, illustrating the extension member of the splint and the concave channel curvature of the splint for closely matching the cylindrical shape of a digit.

FIG. 4 is a side elevation of an alternative embodiment of the splint of FIG. 1 having a tip bent to hold the upper flange of the digit in a downward position toward the palm and shown applied to a digit.

FIG. 5 is a side elevation of the alternative embodiment of FIG. 1 having a tip bent upward relative to the normal straight line of the finger, that is, as opposed to the direction that the knuckle normally bends.

FIG. 6 is a rear elevation of an alternative embodiment of the finger splint of FIG. 1 for use in splinting four or fewer fingers on one hand.

FIG. 7 is a front elevation of the splint of FIG. 6.

FIG. 8 is a top plan view of the splint of FIG. 6.

DETAILED DESCRIPTION OF THE PREFERRED EMBODIMENTS

Figure 9:
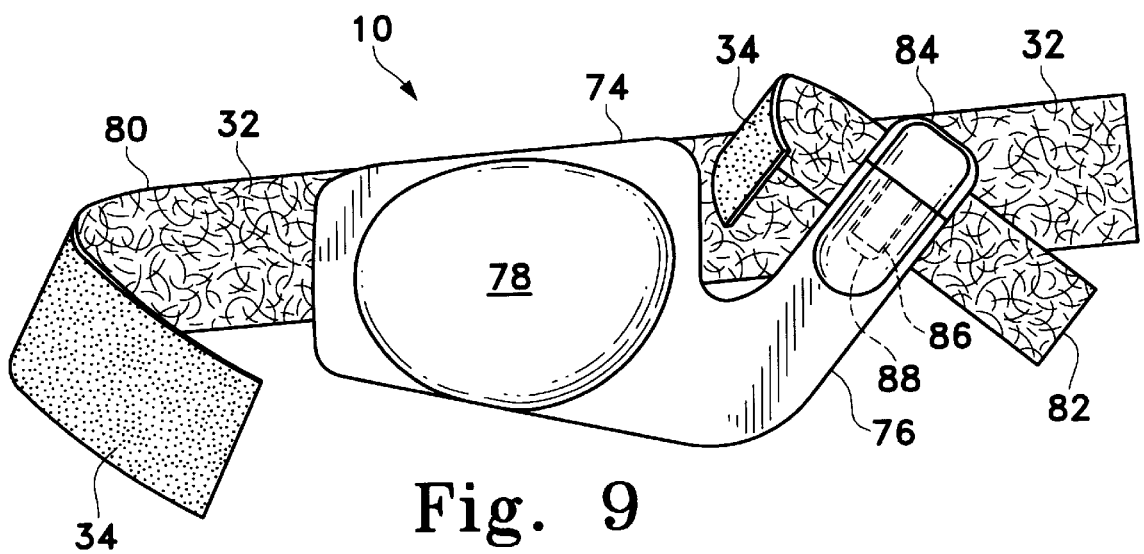
FIG. 9 is rear elevation of a digit splint according to the present invention specially adapted for use on the thumb digit.

As required by the Patent Statutes and the case law, the preferred embodiment of the present invention and the best mode currently known to the inventor for carrying out the invention are disclosed in detail herein. The embodiments disclosed herein, however, are merely illustrative of the invention, which may be embodied in various forms. Therefore, specific structural and functional details disclosed herein are not to be interpreted as limiting, but merely to provide the proper basis for the claims and as a representative basis for teaching one skilled in the art to which the invention pertains to make and use the apparatus disclosed herein as embodied in any appropriately specific and detailed structure.

Referring now to FIGS. 1 and 3, there is shown a splint system for one or more digits of the hand 10, or splint system 10, for one finger having a bulbous base 12 and a splint member body 14 consisting of a single member. A splint member is that portion of the splint system 10 that will splint or support one digit, and each splint member also includes a splint body. The elongated splint member body 14 includes an elongated channel recess 16, which is roughly a portion of a cylinder, for receiving and conforming to the basically cylindrical shape of a finger, thereby providing more support than a flat surface would, as the elongated channel recess 16 cradles the finger. The elongated channel recess 16 faces toward the view in FIG. 1 and is against the finger in FIG. 2. An extension member tip 18 includes a depending tongue member 20 that is received for reciprocal movement in an extension member tongue receiving channel 22 in the splint member body 14. By sliding the extension member tongue up or down within the receiving channel 22, a medical care worker or a patient can adjust the length of the overall splint member 23 to fit different lengths of fingers. The fit between the extension tongue member 20 and the extension member tongue receiving channel 22 is firm enough to allow easy adjustment but to retain a desired length adjustment through frictional engagement of the parts. The extension tip member includes an extension member channel recess 24 that aligns with and continues the channel recess 16 in the splint member body 14.

Figure 10:
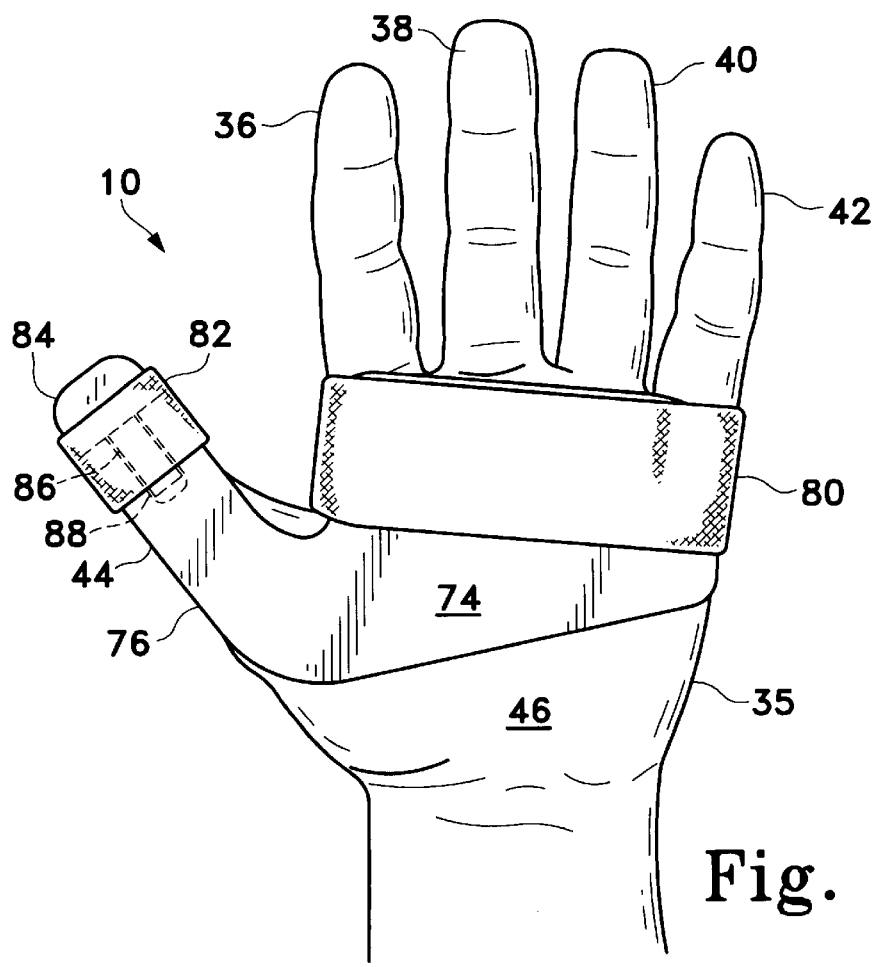
FIG. 10 is a front elevation of the thumb splint of FIG. 9 shown attached to a left hand.

Referring to FIGS. 1, 2, and 3, the splint system 10 also includes a plurality of fastening straps for securing the splint system 10 to the finger and hand. Although a left hand is illustrated in FIGS. 2, 7, 10, and 12, the embodiments of the invention illustrated in FIGS. 1–8 may be used on either hand without modification, while the embodiment illustrated in FIGS. 9 and 10 is provided in left-handed and right-handed models, which are merely mirror images of each other. A short hook and loop fastener strip 28 located toward the upper end of the splint system wraps around the upper end of the finger, such as the middle finger 38 in FIG. 2; a long hook and loop fastener strip 30 wraps around the hand 35 across the palm 46; and an intermediate length hook and loop fastener strip 28 wraps around the first phalange of the middle finger 38. Each of the hook and loop fasteners trips 26, 28, and 30 includes a hook portion 32 and a loop portion 34 so that each strip can be fastened to itself and the tension on each strip can be adjusted to a comfortable firmness that fully supports the splinted digit. The fastener strips 26, 28, and 30 are attached to the overall splint member 23 by an adhesive, with the fastener strips 28, 30 being fastened to the splint member body 14 and the fastener strip 26 being fastened to the extension tip member 18. Alternatively, the fastener strips 26, 28, and 30 may be held in place only by frictional engagement with the treated digit without being permanently fastened to the splint system 10.

Referring now to FIGS. 4 and 5, the splint system in an alternative embodiment is constructed as described above with one change, which is that the installed extension member tip 18 is bent away from the straight line axis of the splint member body 14. In FIG. 4, the splint system 14 further includes an inward bend 48 at the juncture of the finger retaining portion 50 of the extension tip member 18 and the extension member tongue 20, so that the third phalange 52 of the finger 36 is bent forward toward the palm when the splint system 10 is fastened to the finger 36, which is illustrated as the index finger, although this splint system 10 could be used on any digit. In FIG. 5, an outward bent 54 is formed at the juncture of the finger retaining portion 50 of the extension tip member 18 and the extension member tongue 20, so that the third phalange 52 of the finger 36 is bent rearward away from the palm and toward the back of the hand when the splint system 10 is fastened to the finger 36, which is illustrated as the index finger, although this splint system 10 could be used on any digit. In a variety of injury and health situations, it is sometimes necessary to bend the third phalange 52 of one or more fingers either outward or inward during the healing process in order to insure that the healed finger will be straight. The embodiments of the splint system illustrated in FIGS. 4 and 5 are designed to achieve the healing of a damaged finger into a final straight position.

Referring now to FIGS. 6, 7, and 8, an alternative splint system 10 has been adapted for splinting of the four principal fingers of either hand. A basically U-shaped splint body 56 includes four finger receiving channels 58 like those described above, and four extension tip member 60, each having an extension member tongue 62 that is received in a respective extension member tongue receiving channel 64 in the upper end of the splint body 56. A bulbous base portion 66 of the splint body 56 fills the hollow of the palm 46, allowing the fingers 36, 38, 40, and 42 to be splinted straight relative to the general orientation of the hand. Finger 36 is the index finger, finger 38 is the middle finger, finger 40 is the ring finger, finger 42 is the pinkie finger, and finger 44 is the thumb. The hook and loop fastener strap 68 fastens the splint system 10 to the fingers 36, 38, 40, and 42 together and the hook and loop fastener strap 70 fastens the splint system 10 to palm 46 by passing about the palm 46 and the back of the hand. The fastener straps 68 and 70 operate as described above. The use of the extension tip members 60, their seating in the extension member tongue receiving channels 64 and their adjustment are as described above. This allows a splint body having a substantially straight line top edge 70 and one basic size to be used with different hands of substantially different sizes. As shown in FIG. 6, for example, the upper tips of the extension members 60 form a straight horizontal line, but when installed on a hand, as shown in FIG. 7, the lengths of each finger supporting portion of the splint system 10 are different as the amount of extension is adjusted to match the length of each finger. The splint body 56 includes four elongated parallel channel recesses 16, and each extension tip member 60 also includes an extension member channel recess 24 for receiving and cradling each of the four splinted fingers, as described above relative to FIGS. 1,2 and 3. In FIG. 7, these channels 16, 24 are not seen because they are against the palm side of the left hand 35.

Referring now to FIGS. 9 and 10, a splint system 10 specially adapted for splinting the thumb digit 44 includes a trapezoidally shaped base portion 74 having a thumb retaining extension portion 76, which lies at an angle in the range of 40–60 degrees measured in a clockwise direction from a horizontal line through the lowest point of the extension portion 76, with the preferred angle being 50 degrees. This orientation allows the thumb digit to be splinted at a natural angle to the hand. The trapezoidally shaped base portion 74 has protruding basically circular palm pad 78 that fills the hollow of the palm 46 of the left hand 35, allowing the trapezoidally shaped base portion 74 to lie basically flat across the palm side of the left hand 35, while remaining comfortable for the user and keeping the base portion of the hand flat. A palm encompassing strap 80 and a thumb encompassing strap 82 secure the splint system 10 to the hand 35 and thumb 44 in the manner described above. An extension tip member 84 includes an extension member tongue 86 that fits snugly into an extension member tongue receiving slot 88 for length adjustment as described above. The embodiment of the splint system 10 shown in FIGS. 9 and 10 enables the thumb 44 to be splinted into a position basically flat and aligned with the plane of the palm 46, and at a natural angle lying in the range of about 40–70 degrees relative to a horizontal line drawn through the lower base of the palm portion of the hand, with the preferred angle in most cases being 45 degrees. To provide a thumb splint system 10 for the right hand, the front of the splint system 10 (which faces the view as shown in FIG. 9), becomes the rear (shown in FIG. 10) and the basically circular palm pad 78 is placed on the obverse surface of the trapezially shaped base portion 74.

Figure 11:
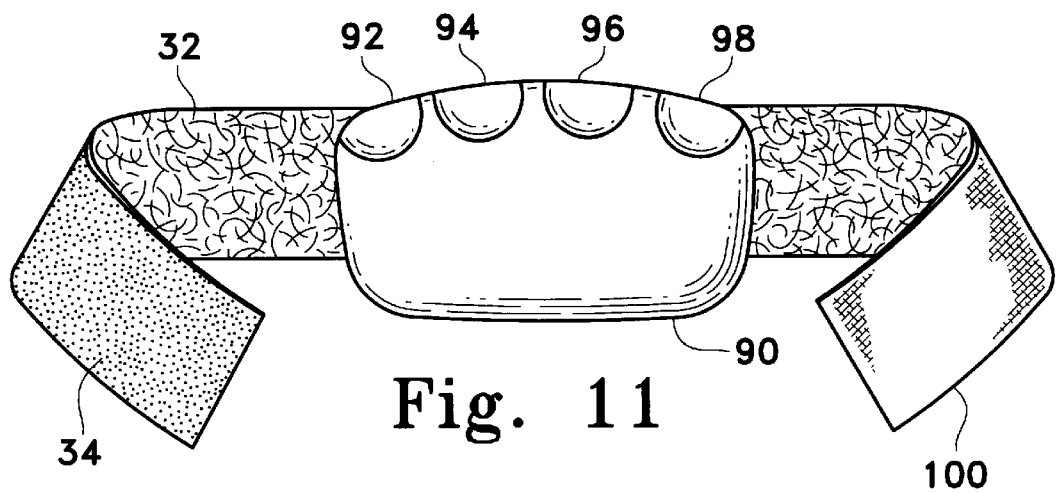
FIG. 11 is a front elevation of the finger restraining splint system according to the present invention.
Figure 12:
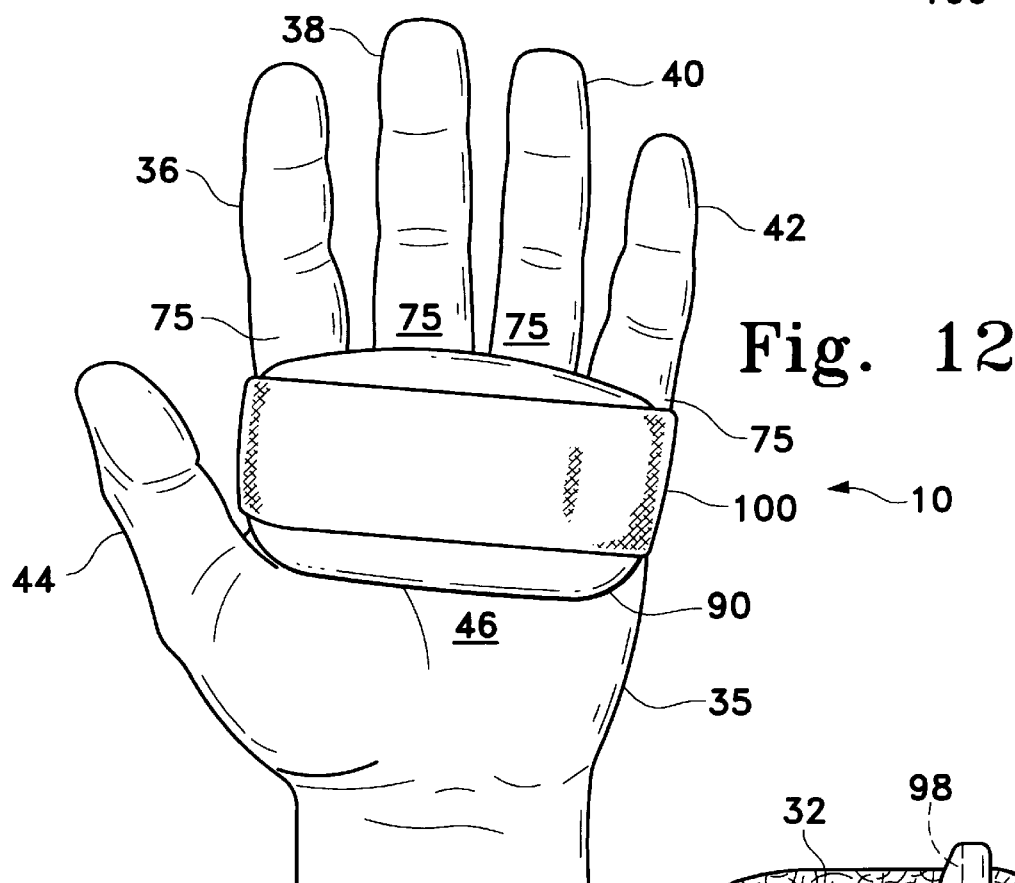
FIG. 12. is a front elevation of the splint system of FIG. 11 shown in use on a left hand.
Figure 13:
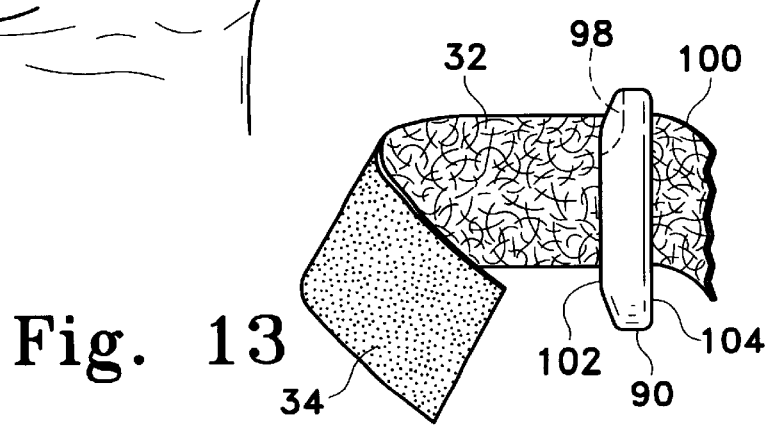
FIG. 13 is a right-hand side elevation of the splint system of FIG. 11.

Referring now to FIGS. 11–13, it is sometimes necessary or desirable to provide support for the bases 75 of the fingers 26,38,40 and 42, particularly in the elderly, to prevent the fingers from permanently curling into the palm 46. The embodiment shown in FIGS. 11–13 is specially adapted for this purpose. The splint system 10 includes a base 90 shaped to conform to the shape of the palm 46 and include indentations for receiving the bases of the fingers 75 (FIG. 12), with indentations to support the bases of the fingers. The indentations 92, 94, 96 and 98 are basically semi-cylindrical in shape and are angled to align with the natural directional orientation of the fingers of normally arranged fingers. The indentation 98, which receives the index finger 36, has a central longitudinal axis that lies at an angle in the range of 65–75 degrees, with the preferred angle being 70 degrees. The indentation 96, which receives the middle finger 38, has a central longitudinal axis that lies at an angle in the range of 85–95 degrees, with the preferred angle being 90 degrees. The indentation 94, which receives the ring finger 40, has a central longitudinal axis that lies at an angle in the range of 105–110 degrees, with the preferred angle being 100 degrees. The indentation 92, which receives the pinkie finger 42, has a central longitudinal axis that lies in the range of 120–130 degree, with the preferred angle being 125 degrees. All angles at measured along a counterclockwise path from a horizontal line through the base of each indentation 92, 94, 96, and 98.

A strap 100, which includes hook portions 32 and loop portions 34 of a hook and loop fastener system, is wrapped about the splint system 10 to secure it to the hand 35. A convex palm facing surface 102 provides fills the hollow of the palm 46, while the obverse side made by flat. The strap 100 may be permanently fastened to the flat side 104 of the base 90.

The invention made be made of injection molded plastic or other convenient materials. The straps are preferably made from fabric. They may be attached to the respective embodiments by any suitable adhesive, or they may be unattached and held in position during use by the frictional engagement of the fastening system, which may be any convenient system, such as the hook and loop fasteners described herein, or by buckles or the like.

While the present invention has been described in accordance with the preferred embodiments thereof, the description is for illustration only and should not be construed as limiting the scope of the invention. Various changes and modifications may be made by those skilled in the art without departing from the spirit and scope of the invention as defined by the following claims.

I claim:

1. A splint system for one digit of the hand comprising:
   a. a splint member comprising a splint body having an upper end and a base portion wider that said splint body and a depending tongue member receiving channel in said upper end of said splint body aligned with a longitudinal axis of said splint body, said depending tongue member receiving channel extending downwardly from said upper end of said splint body within a range of from one-third to one-half of the length of said splint body; and b. an extension tip member having a depending tongue member slidably received in said slot of said splint body with sufficient frictional engagement between said depending tongue member receiving channel and said depending tongue member of said extension tip to maintain said extension tip in a desired position relative to said splint body such that when placed on the hand of a user, the splint member is adapted to extend only from the metacarpals to the proximal phalange which it covers.

2. A splint system for one digit of the hand in accordance with claim 1 wherein said base of said splint body further comprises a bulbous base that is wider than the width of said splint body.

3. A splint system for one digit of the hand in accordance with claim 2 wherein said bulbous base further comprises a wider portion on an inner surface of said splint body.

4. A splint system for one digit of the hand in accordance with claim 2 wherein said bulbous base is adapted to fit within the palm of a hand.

5. A splint system for one digit of the hand in accordance with claim 1 wherein said splint body and said upper tip extension member both further comprise a concave surface running from a point adjacent to an outer end of said extension tip to a point along said splint body below and adjacent to a middle finger joint contact point for conforming to the shape of a finger.

6. A splint system for one digit of the hand in accordance with claim 1 further comprising a means for fastening said finger splint to said finger.

7. A splint system for one digit of the hand in accordance with claim 6 wherein said fastening means further comprises a plurality of straps having hook and loop fasteners attached to each said strap such that each said strap may be fastened to itself.

8. A splint system for one digit of the hand, comprising:

a. a splint member comprising a splint body having an upper end and a bulbous base adapted to fit within the palm of a hand, and a slot in said upper end of said splint body aligned with a longitudinal axis of said splint body; and b. an extension tip member having a tongue slidably received in said slot of said splint body.

9. A splint system for one digit of the hand in accordance with claim 1 wherein said extension tip member further comprises a tip member bent away from a straight line axis of said splint member body.

* * * * *